US012533528B2

(12) United States Patent
Voet et al.

(10) Patent No.: US 12,533,528 B2
(45) Date of Patent: Jan. 27, 2026

(54) SYSTEM AND METHOD FOR RADIATION TREATMENT PLANNING

(71) Applicant: Elekta, Inc., Atlanta, GA (US)

(72) Inventors: Peter Voet, Atlanta, GA (US); Chunhua Men, Atlanta, GA (US); Randy Larson, Atlanta, GA (US); Spencer Marshall, Brandon, FL (US)

(73) Assignee: Elekta, Inc., Atlanta, GA (US)

( * ) Notice: Subject to any disclaimer, the term of this patent is extended or adjusted under 35 U.S.C. 154(b) by 280 days.

(21) Appl. No.: 18/315,974

(22) Filed: May 11, 2023

(65) Prior Publication Data

US 2024/0374926 A1 Nov. 14, 2024

(51) Int. Cl.
*A61N 5/10* (2006.01)

(52) U.S. Cl.
CPC .................................. *A61N 5/1031* (2013.01)

(58) Field of Classification Search
CPC .................................................... A61N 5/1031
See application file for complete search history.

(56) References Cited

U.S. PATENT DOCUMENTS

| | | | |
|---|---|---|---|
| 6,064,203 | A | 5/2000 | Bottomley |
| 6,963,771 | B2 | 11/2005 | Scarantino et al. |
| 7,317,192 | B2 | 1/2008 | Ma |
| 8,492,735 | B2 | 7/2013 | Brand |
| 9,884,206 | B2 | 2/2018 | Schulte et al. |
| 10,737,114 | B2 | 8/2020 | Gattiker et al. |
| 10,835,760 | B2 | 11/2020 | Kuusela et al. |
| 2015/0202464 | A1 | 7/2015 | Brand et al. |
| 2018/0154177 | A1 | 6/2018 | Bzdusek et al. |
| 2018/0304099 | A1 | 10/2018 | Li et al. |
| 2021/0138267 | A1 | 5/2021 | Nord et al. |
| 2021/0316157 | A1 | 10/2021 | Lynch et al. |
| 2021/0379404 | A1 | 12/2021 | Basiri et al. |

FOREIGN PATENT DOCUMENTS

| | | |
|---|---|---|
| EP | 3681600 | 7/2020 |

OTHER PUBLICATIONS

Elekta AB, “”, Monaco Training Guide, Document ID: LTGMON0530, (2017), 1313 pgs.

“European Application No. 24175407.6, Extended Search Report dated Sep. 9, 2024”, (Sep. 9, 2024), 7 pgs.

*Primary Examiner* — Mark R Gaworecki

(74) *Attorney, Agent, or Firm* — Schwegman Lundberg & Woessner, P.A.

(57) ABSTRACT

A computer-implemented method for radiation treatment planning, the method comprising: receiving a reference dose value, wherein the reference dose value is a defined maximum radiation dose within a first region for radiation treatment in a patient; applying an optimization procedure to a treatment plan for radiation treatment of the patient, wherein the optimization procedure seeks to minimize a cost function which is representative of a dose excess value above the reference dose value; and responsive to determining that the dose excess value is below a threshold value: decreasing the reference dose value; and reapplying the optimization procedure to the treatment plan, wherein the optimization procedure seeks to minimize the cost function based on the decreased reference dose value.

23 Claims, 6 Drawing Sheets

SYSTEM AND METHOD FOR RADIATION TREATMENT PLANNING

TECHNICAL FIELD

Embodiments of the present disclosure relate to systems and methods for treatment planning for delivering radiation therapy. More specifically, embodiments of the disclosure relate to a computer-implemented method for radiation treatment planning, and data processing apparatuses, computer programs, and non-transitory computer-readable storage mediums configured to execute methods for radiation treatment planning.

BACKGROUND

Radiotherapy or radiation therapy is the use of ionising radiation, such as X-rays or charged particles, to damage or destroy unhealthy cells in a human or animal body. During treatment, the ionising radiation is formed into a beam and directed to unhealthy cells in the body, such as a tumour. The cells to be treated may be deep inside the body or near the surface, e.g., in the skin.

The delivered dose distribution depends on treatment parameters such as the beam direction, dose per beam, number of beams, beamlet weights, and exposure time. Radiation treatment planning is the process of determining a set of treatment parameter values that will provide the required treatment with minimal damage to the surrounding healthy tissue. Treatment planning may be performed using a treatment planning system, such as Monaco®.

Whilst an "ideal" dose distribution would be the delivery of at least the minimum required dose to the unhealthy cells and zero dose to the healthy cells, in reality some dose to the surrounding healthy tissue is inevitable. The aim of treatment planning is therefore to optimise the delivered dose distribution so that the unhealthy cells receive at least the minimum required dose, and the healthy cells receive as little dose as possible, particularly any sensitive or at-risk anatomical parts. An optimisation procedure is performed to determine a set of optimum parameters that would deliver a suitable dose. The optimisation procedure may be subject to clinical and dosimetric objectives and constraints. For example, the objectives and constraints could specify maximum, minimum and/or mean radiation doses for different regions of the body. Constraints are conditions that must be met, such as a minimum dose to the region comprising the tumour. The objectives are goals to be achieved. For example, an objective could be that the dose delivered to a certain region comprising healthy tissue does not exceed a maximum radiation dose, also referred to as a reference dose. Objectives and constraints can also relate to any other treatment parameter, such as beamlet weights, number of radiation beamlets, range of movement of the radiotherapy equipment, etc.

During treatment planning, an anatomical region of the patient is modelled using a three-dimensional image of the patient, e.g., a computed tomography (CT) image. Image segmentation is performed to define different regions within the image, referred to as segments. Different objectives and constraints may be defined for different segments. The properties used to delineate the segments could, for example, include any property that influences dose requirements, such as tissue type, cell health, sensitivity to radiation, anatomy, and organ functionality. A region identified as needing treatment (e.g., a region comprising a tumour) is referred to as a clinical target volume (CTV). A region to which treatment is to be delivered is referred to as the planning target volume (PTV) and is typically the CTV plus some margin that is added to help ensure that the CTV is treated effectively. A region in which a treatment dose is undesirable is referred to as an organ at risk (OAR).

The aim of the optimisation problem is to determine a radiation treatment plan that, to the extent possible, satisfies the constraints and objectives.

Treatment planning is a time consuming and complex process. Therefore, there is a need for improved methods and systems for generating treatment plans.

SUMMARY

A treatment plan can be optimised by minimising a cost function which provides a measure of the extent to which an objective is satisfied by a dose distribution achieved by the treatment plan. For example, an overdose cost function provides a measure of the difference between a dose achieved by the treatment plan (e.g., the dose in an anatomical region) and a reference dose (e.g., a maximum acceptable dose in that region). A cost function is calculated for a particular region of the body, e.g., a region comprising a PTV or an OAR. The optimisation procedure seeks to minimise the cost function by adapting the treatment plan subject to the relevant objectives and/or constraints.

However, problems can arise with this optimisation approach. When the dose achieved by the treatment plan is equal to, or less than, the reference dose, the cost function is zero. At this point, the cost function cannot be reduced any further by optimisation, and therefore the cost function becomes idle. However, in many cases, the cost function becomes idle before the treatment plan has been fully optimised. In other words, although the dose delivered to the OAR is equal to or less than the reference dose, it is still possible to reduce the dose by further adapting the treatment plan. In these cases, the opportunity to further improve the treatment plan may be missed.

Embodiments of the disclosure seek to address this problem by providing a computer-implemented method for radiation treatment planning in which, when the optimisation procedure provides a treatment plan (or dose distribution) with a dose excess value that is below a threshold value, the reference dose value is decreased. Thus, the method prevents the cost function becoming idle and enables the treatment plan to be further optimised.

According to a first aspect, there is provided a computer-implemented method for radiation treatment planning. The method comprises receiving a reference dose value, where the reference dose value is a defined maximum radiation dose within a first region for radiation treatment in a patient. The method further comprises applying an optimization procedure to a treatment plan for radiation treatment of the patient. The optimization procedure seeks to minimize a cost function which is representative of a dose excess value above the reference dose value. The method further comprises, responsive to determining that the dose excess value is below a threshold value: decreasing the reference dose value; and reapplying the optimization procedure to the treatment plan. This optimization procedure seeks to minimize the cost function based on the decreased reference dose value.

According to a second aspect, there is provided a data processing apparatus comprising a memory storing computer-executable instructions and a processor. The processor (or controller circuitry) is configured to execute the instructions to carry out the method of the first aspect.

According to a third aspect, there is provided a computer program comprising instructions which, when the program is executed by a computer, cause the computer to carry out the method of the first aspect.

According to a fourth aspect, there is provided a non-transitory computer-readable storage medium comprising instructions which, when executed by a computer, cause the computer to carry out the method of the first aspect.

Thus, the present disclosure provides an improved method for radiation treatment planning. The disclosed method provides treatment plans which deliver a reduced dose to OARs compared to existing methods. These benefits are achieved in an automated manner that does not require user interaction. Advantageously, the techniques can be applied to a wide variety of patients and anatomies and allows improved treatment plans to be determined for each individual patient.

Embodiments of the disclosure may be implemented in digital electronic circuitry, or in computer hardware, firmware, software, or in combinations thereof. Embodiments of the disclosure may be implemented as a computer program or a computer program product, i.e., a computer program tangibly embodied in a non-transitory information carrier, e.g., in a machine-readable storage device or in a propagated signal, for execution by, or to control the operation of, one or more hardware modules. A computer program may be in the form of a stand-alone program, a computer program portion, or more than one computer program, and may be written in any form of programming language, including compiled or interpreted languages, and it may be deployed in any form, including as a stand-alone program or as a module, component, subroutine, or other unit suitable for use in a data processing environment.

The disclosure is set out herein in terms of particular embodiments. Other embodiments, not explicitly described here, may nonetheless fall within the scope of the claims. Unless explicitly or implicitly specified otherwise, the steps of methods according to embodiments of the disclosure may be performed in a different order and still achieve desirable results.

BRIEF DESCRIPTION OF THE DRAWINGS

Exemplary embodiments will now be described, by way of example only, with reference to the following drawings, in which.

DETAILED DESCRIPTION OF EMBODIMENTS

Figure 1A:
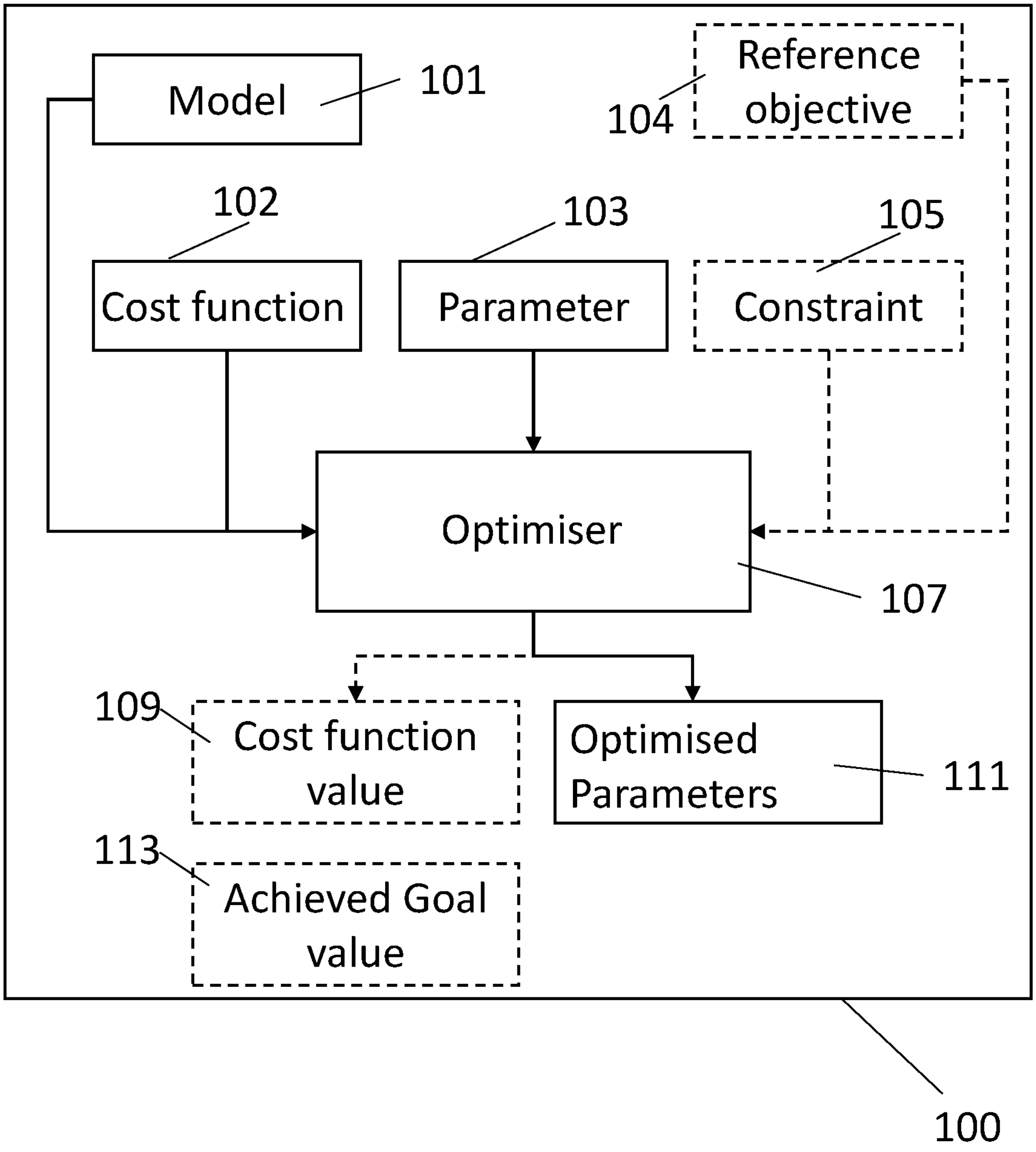
FIG. 1A is a block diagram showing an optimisation procedure according to various embodiments of the present disclosure.

FIG. 1A is a block diagram showing an optimisation procedure 100 for determining a set of parameters (i.e. one or more parameters) that define a radiotherapy treatment plan for a radiotherapy system. An example of a radiotherapy system is described with reference to FIG. 5.

The optimisation module 100 comprises an optimiser 107 configured to receive at least: a model 101, a cost function 102 and one or more parameters 103. Optionally, the optimiser 107 may also receive a constraint 105 and/or a reference objective 104. The optimisation module 100 performs an optimisation procedure and outputs a set of optimised parameters 111 that minimise the cost function 102. The optimised parameters 111 are values for the one or more parameters 103 that were inputted into the optimiser 107. The optimisation module 100 may also output one or both of a cost function value 109 (the cost function 102 evaluated with the optimised parameters 111) and an achieved goal value 113 (for comparison with the reference objective 104).

The optimiser 107 uses at least one optimisation algorithm such as a simplex algorithm, a gradient-based algorithm, or an interior point algorithm, etc., or a combination thereof. Those skilled in the art will appreciate that other optimisation algorithms are also possible and the present disclosure is not limited to any particular optimization algorithm. Examples of optimization are provided in Monaco® Training Guide, Document ID: LTGMON0530 (Elekta AB). The optimisation procedure may, for example, correspond to the optimisation procedure described in European patent application publication EP3681600A1.

The model 101 is a representation of an anatomical region to be treated. For radiotherapy treatment planning, the anatomical region may comprise one or more anatomical regions (i.e., subregions), such as one or more of: a target region, a region of healthy tissue (OAR), planned target volume, critical structures, or shell structures. These regions or structures may be determined or defined by performing image segmentation of a three-dimensional image or model of the anatomical region. Shell structures are structures generated to tune the dose delivered to the tissue surrounding the target, and they may be used to control dose conformality.

The cost function 102 is a mathematical formulation that provides a measure of the extent to which the reference objective 104 (e.g., one or more objectives) is satisfied by a set of parameters 103. The cost function 102 evaluates a dose distribution over a region of the model 101 based on the set of parameters 103. The region may be divided into voxels, and the dose calculated per voxel. The dose distribution may be calculated using pencil beam algorithms, convolution-based algorithms and/or Monte Carlo (MC) based algorithms. The dose distribution is described in more detail with reference to FIG. 1B, and further details of how the dose may be determined are provided in Monaco® Training Guide, Document ID: LTGMON0530 (Elekta AB).

The cost function 102 relates the dose distribution to a single value, referred to as a cost function value 109. The cost function 102 may define a penalty for violating one or more objectives. The cost function may also be referred to as an objective function.

The cost function 102 is evaluated by the optimiser 107 during optimisation. The optimisable parameters 103 are varied by the optimiser 107 so as to minimise the cost function 102. Optionally, in constrained optimisation, the constraint 105 does not contribute to the cost function, instead a violation of a constraint 105 results in the rejection of the treatment plan. For example, the reference objective may be a mean dose to a healthy organ (such as the bladder) of less than a dose value (e.g., 30 Gy), and the constraint may be a maximum dose to the patient (as a whole) of less than another dose (e.g., 50 Gy). The cost function may provide a mathematical formulation for calculating the mean dose to the bladder, and the optimiser aims to obtain the reference objective (a dose to the bladder of less than 30 Gy) subject to the constraint. The optimised solution provided by the optimiser may comprise a dose to the bladder that is less than or greater than 30 Gy, but if the optimiser cannot find a solution in which the maximum dose to the patient is less than 50 Gy, then no solution (e.g., no treatment plan) will be provided. A constraint may in some cases be referred to as a special type of cost function that cannot be violated (and therefore the value of the cost function is immaterial), however such terminology is not used herein.

The one or more parameters 103 are optimisable parameters (also referred to as decision variables or treatment parameters) for which the optimiser 107 attempts to find optimum values. The optimisable parameters 103 may relate to characteristics of the radiation to be delivered by the radiotherapy system. For example, the optimisable parameters 103 may include one or more of: beamlets weights, beam angles, dose-histogram-volume information, the number of radiation beams, dose per beam, and a dose excess value (e.g., a root mean square dose excess above a reference dose). The one or more parameters 103 may be initialised to a predetermined set of values, e.g., a "best guess" set of values or an arbitrary set of values. Alternatively, the parameters 103 may be initialised to values determined in a previous step. For example, when multiple optimisations are performed, the parameters may be initialised to values determined in a previous optimisation procedure (e.g., based on a different reference objective 104).

The constraint 105 comprises one or more conditions that the optimised parameters 111 must satisfy. The constraint 105 may include one or more hard constraints (conditions that the parameters 111 are required to satisfy). Constraints restrict the set of possible solutions and can be used to define what is physically possible and/or clinically acceptable. Note that the constraint 105 is an optional feature.

The reference objective 104 comprises a goal that the optimiser tries to achieve. For example, the reference objective may relate to a dose-based objective and/or a volume-based objective. A dose-based objective may comprise a dose value (in Gy), e.g., a maximum, minimum or mean dose for a given region of the model 101. A volume-based objective may comprise a relative volume (e.g., a fraction/percentage of a volume of a region of the model 101) or an absolute volume. The absolute volume may be defined in terms of physical dimensions (e.g., in mm, cm, $mm^3$, $cm^3$, etc. . . . ). For example, a reference objective 104 may require that at least X % of a first region receives at least Y Gy during the treatment.

Additionally, the reference objective 104 may comprise an indication of the cost function 102 to be used. The reference objective 104 may also comprise an indication of an anatomical structure to which a goal to be achieved is applicable, e.g., the region of the model 101 to which a maximum/minimum/mean dose applies. The optimiser 107 will determine a set of optimised parameters 111 that result in an achieved goal value 113 that is close to the reference objective 104. Note that the reference objective 104 is an optional feature.

Thus, the reference objective 104 is an anatomy-specific function that establishes the dose and/or biological response goal, and constraints 105 are anatomy-specific functions that may be hard or soft. When constraints are used together with objectives, the constraints are hard constraints that must be met. Conversely, objectives are goals that the optimiser 107 tries to achieve.

The cost function 102, together with the model 101, the parameters 103, the constraint 105 (optional) and the reference objective 104 (optional), define the problem to be solved. The term "treatment-planning objective" may refer collectively to all aspects of the reference objective 104 and/or constraint 105. For example, each of row m to x in Table 1 below represents a treatment-planning objective and sets out: the type of constraint; the layering order; the relevant structure of the model to which the constraint applies; the cost function to be used; and a goal to be achieved.

As noted above, the optimiser 107 aims to find a set of optimised parameters 111 for which the cost function 102 is minimised. The optimised parameters 111 are an output of the optimiser 107. In an example, when a reference objective 104 is present, the optimiser 107 minimises a difference between the goal value 113 and a reference objective 104.

Optionally, the optimiser 107 outputs the cost function value 109. The cost function value 109 is the value of the cost function 102, when evaluated with the optimised parameters 111.

Optionally, the optimiser 107 outputs an achieved goal value 113. An achieved goal value 113 typically has the same units as a reference objective so that it can be compared to the reference objective 104. The achieved value 113 may be different from the cost function value 109. Unlike the cost function value 109, which may be a number that is an evaluation of the cost function, the achieved value 113 may have a physical meaning. In an example, when the reference objective 104 comprises a dosimetric objective in Gray (Gy), the achieved goal value 113 also relates to a dose (i.e. it has the units of Gy and/or the same physical meaning as the reference objective 104). In a further example, when the reference objective 104 comprises a reference volume and a dose value, the achieved goal value also relates to a reference volume and a dose value (i.e. it has the same physical meaning as the reference objective). As will be described below in relation to Table 1, a reference objective 104 might be dose-volume histogram (DVH) based and may be a goal for a percentage of a volume to receive a predetermined dose. The achieved goal value 113 would be the achieved percentage of the volume that receives the predetermined dose. In other words, the achieved goal value 113 can be compared to the reference objective 104.

The optimisation procedure 100 may be repeated for one or more different reference objectives 104. In other words, the treatment planning may be divided into a series of optimisation problems, with each optimisation problem focusing on a specific goal (i.e., reference objective 104), and optionally subject to one or more constraints. The different reference objectives 104 may, for example, relate to different (or overlapping) anatomical regions (or shells or structures) within the patient. The output of a first optimisation procedure 100 may contribute to a second optimisation procedure 100. For example, the reference objective 104 of a previous optimisation procedure may be set as a constraint 105 for a subsequent optimisation procedure. In such cases, the reference objectives 104 may have corresponding priority levels so that the order in which the optimisation problems are solved may be determined based on their corresponding priority levels. Thus, the optimisation procedure 100 may be performed for the reference objective 104 with the highest priority level first, and subsequent optimisation procedures may be performed in order of decreasing priority. If a reference objective 104 cannot be met, the reference objective 104 may be revised, and the optimisation repeated using the revised reference objective 104.

As an example, the optimisation procedure 100 illustrated in FIG. 1A, can be applied to intensity-modulated radiation therapy (IMRT). In IMRT, one or more radiation beams are directed to a tumour, and the intensity of each beam profile is non-uniform. In this example, the optimisation process 100 of FIG. 1A is performed to determine the weights of the radiation beamlets (and the weights correspond to the parameters 103). The cost function 102 comprises a mathematical expression relating a dose distribution at unit fluence to the beamlet weights 103. The cost function 102 incorporates a reference objective 104 which sets out a maximum dose (i.e. reference dose) for a first region of the model 101 comprising an OAR. If the dose in the first region exceeds the maximum dose, a penalty is incurred in the cost function 102 (i.e., the value of the cost function 102 increases). The cost function 102 further incorporates a hard constraint 105 that the beamlet weights cannot be negative (since a negative beamlet weight is not possible). The output of the optimisation procedure 100 comprises the optimised beamlet weights 111.

Although the above example applies to IMRT, it is noted that optimisation procedure 100 may be applied to other modes of radiotherapy.

The optimisation procedure 100 may be part of a first stage of the treatment planning process in which a radiation fluence map (or intensity map) is optimised. A fluence map is indicative of the expected radiation dosage across a region in accordance with the radiation treatment plan. The first stage may comprise one or more optimisation procedures 100, e.g. corresponding to one or more reference objectives 104.

The first stage may then be followed by a second stage in which the optimised parameters 111 from the first stage are used to determine a configuration for the treatment planning system that is to perform the treatment. Both the first stage and the second stage are described in more detail with reference to FIG. 1B.

It will be understood that the techniques disclosed herein are not limited to the two-stage approach described with reference to FIG. 1B.

Figure 1B:
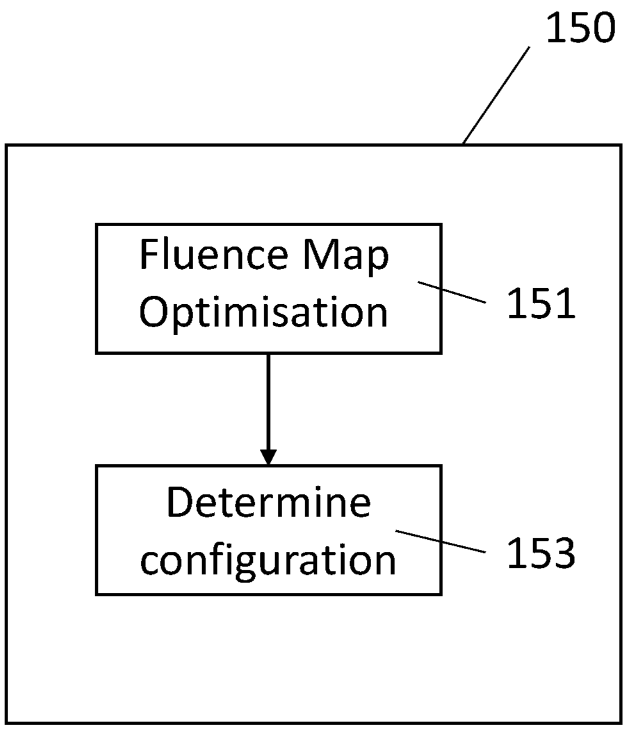
FIG. 1B is a block diagram showing a two-stage optimisation procedure according to various embodiments of the present disclosure.

FIG. 1B is a block diagram illustrating a two-stage optimisation procedure 150. The procedure 150 is described herein with reference to IMRT treatment planning, but it may also be applied to volumetric modulated arc therapy (VMAT). Furthermore, it is noted that the optimisation procedure 150 may also be applied to other modes of radiotherapy.

The aim of the optimisation procedure 150 is to modify the IMRT beam intensity profile such that a high enough dose is delivered to the tumour, while reducing the dose delivered to healthy organs.

The method of optimisation for IMRT 150 comprises two stages. The first stage (step 151) is fluence map optimisation (FMO) and the second stage (step 153) is the determination of a configuration of the radiotherapy system. In FMO 151, an optimal fluence map is determined. The optimal fluence map is then used to determine a configuration for the radiotherapy system in step 153.

For fluence optimisation 151, each beam is divided into a number of beamlets. The contribution of each beamlet, at unit fluence, to voxels is then calculated. During optimisation, the weight of each beamlet is adjusted such that a cost function is minimised. By multiplying the weight with the contribution of each beamlet at unit fluence, the full dose distribution may be obtained. The full dose distribution may be compared with any constraints and/or reference objective to determine if the optimised solution is suitable.

The optimisation procedure for FMO may be performed by the optimisation procedure 100 described with reference to FIG. 1A and further described below.

Optimisation 151 comprises minimizing a cost function $f(x)$ by determining suitable values of parameters x based on certain constraints g. For FMO, the parameters x may correspond to the weight of the beamlets (the parameters x may also be referred to as decision variables). The output of FMO (step 151) comprises optimized values for the parameters x.

The constraints g comprise restrictions. An example of a restriction is a minimum dose at voxels corresponding to a target, or a maximum dose at voxels corresponding to OAR, etc.

In an example, a cost function $f(x)$ is:

$$f(x)=T1+T2+\ldots+T3, \quad \text{(Eqn. 1)}$$

where, e.g., $T1=\Sigma x_n \cdot d_n$, where, when x corresponds to weight of a beamlet, $d_n$ represents the dose that each beamlet gives to a voxel at unit intensity. The voxels are obtained from the model 101 described above, and therefore $d_n$ is associated with the model 101. $d_n$ is a non-optimizable parameter (e.g., it may depend on machine configuration and/or properties of the tissue). In an example, the dose $d_n$ may be determined by pencil beam algorithms, convolution based algorithms and/or Monte Carlo (MC) based algorithms. Optionally, dose calculations use pencil beam algorithms or convolution-based algorithms, which are faster than MC based algorithms but have reduced accuracy, i.e., result in a less realistic dose calculation. Further details of how the dose $d_n$ may be determined are provided in Monaco® Training Guide, Document ID: LTGMON0530 (Elekta AB).

The output of stage 1 (step 151) may include a dose distribution.

In this example, the objective function $f(x)$ is the sum of the total dose (T1, T2 . . . . T3) where each of T1, T2 . . . . T3 represent the dose on different structures. Note that alternative formulations of the problem to be solved (e.g. by defining different cost functions or constraints) may be used.

In an example, the requirement for the dose at a target to be above a certain amount may be formulated as a constraint. Alternatively, such a requirement could be formulated as a reference objective.

Step 151 provides a set of optimised parameters (e.g., beamlet weights x) that would provide an optimum intensity map (or fluence map).

To be ready for delivery by the radiotherapy system, a further step (step 153) is required to translate each optimised beamlet weight into a configuration of the machine that would deliver the optimum fluence.

At step 153, the output from step 151 is turned into a configuration of a radiotherapy system. The configuration is useable by a radiotherapy apparatus (examples of which are described herein) for delivering radiation therapy. For example, the configuration of the radiotherapy system comprises a set of (i.e., one or more) aperture configurations. The shapes and weights of the aperture configurations are selected to meet the same goal as in the first stage. Aperture configurations may be realised by a beam shaping apparatus, such as part 550 of FIG. 5.

An aperture configuration may be referred to as a control point or a segment. The control point and/or segment comprise radiation information (e.g. energy, dose) and geometric information such as gantry angle and leaf position. The shapes and weights of the apertures may be determined by applying algebraic and trigonometric considerations to the arrangement of the aperture in order to implement the optimised beamlet weights of step 151.

Alternatively, step 153 comprises performing a second stage optimisation procedure to determine an optimised aperture configuration that would implement the optimised fluence pattern determined in step 151. The second stage optimisation procedure may be referred to as aperture optimisation, or aperture refinement.

Aperture optimisation may comprise the following:

Receiving a set of beamlet weights (e.g., from step 151)

Performing optimisation to determine optimised aperture shapes and, optionally, weights. The optimisation may be performed using an optimisation procedure such as in FIG. 1A, for example. Other optimisation procedures are possible.

When the beam shaping apparatus comprises a multi-leaf collimator (MLC), aperture optimisation may comprise:

Receiving a set of beamlet weights from FMO and/or fluence profiles (e.g., from step 151)

Converting the received profile into beamlet widths (the opening between a leaf pair). This results in a segment.

Optimising the weights of the resulting segments.

Optionally, optimising shapes of the resulting segments (using a procedure referred to as segment shape optimisation).

Note that the optimisation steps in step 153 may comprise a calculation of the dose distribution. The dose distribution may be calculated using pencil beam algorithms, convolution-based algorithms and/or Monte Carlo (MC) based algorithms. Optionally, dose calculations in step 153 use MC based algorithms (which are more accurate but computationally expensive).

Further details of aperture optimisation are provided in Monaco® Training Guide, Document ID: LTGMON0530 (Elekta AB).

The step of determining a configuration of the radiotherapy system (step 153) is based on at least a set of optimised parameters from stage one (step 151).

While the example of FIG. 1B relates a two-stage optimisation procedure (FMO at step 151 and determination of a configuration at step 153) for IMRT, it is noted that alternative methods of optimisation, such as Direct Machine Parameter Optimisation (DMPO), may be used instead. In DMPO, the decision variable x corresponds to a parameter of a machine (e.g. an MLC leaf position) that delivers radiation.

Returning to the cost function 102 in the optimisation procedure 100, examples of cost functions include: Target EUD, Target Penalty, Quadratic Overdose, Quadratic Underdose, Serial, Parallel, Maximum Dose, Overdose DVH, Underdose DVH. These cost functions are briefly described below. Each cost function offers different calculation methods.

When the cost function comprises any of target penalty, parallel, overdose DVH, and Underdose DVH, the reference objective 104 is a dose value and either a relative volume component (e.g. a percentage) or an absolute volume (e.g. in cc).

When the cost function comprises any of Target EUD, quadratic overdose, serial, maximum dose, or conformality, the reference objective 104 is a dose value.

Cost functions such as serial, parallel, quadratic overdose, overdose DVH, or maximum dose aim to limit the dose at an anatomical structure. Cost functions such as quadratic underdose or underdose DVH aim to increase the dose at an anatomical structure. Cost functions such as Target EUD and Target Penalty aim to increase the dose at a structure. Some of the above cost functions also take a unitless number as input. The unitless number (k) is a power law exponent.

The Target EUD cost function defines a structure as a target volume and expresses the probability that a target cell survives a given dose. This cost function requires a prescribed dose as input (i.e. the reference objective for this cost function is a dose value). The prescribed dose, in Gy, is an equivalent uniform dose (EUD). An EUD is a homogenous dose that, if delivered at an anatomical structure, has the same clinical effect as a non-homogenous dose distribution.

The Target Penalty cost function takes as input a prescribed dose and a minimum volume as input (i.e., the reference objective for this cost function is a dose and a relative volume). The Target Penalty is a quadratic penalty which starts at a threshold dose. It produces steeper dose gradients after a target threshold is met. The Target Penalty is used to define the requirement that at least some fraction of the total anatomical structure volume should receive at least the target dose.

The quadratic overdose (QO) cost function is a cost function used to limit the dose in the structure to which it is applied. The QO may be applied to either targets or OARs. The QO cost function may be used to limit hot spots in a target. The QO cost function takes as input a maximum dose and a maximum root-mean square (RMS) dose excess. The maximum dose defines a dose beyond which a penalty is incurred in the cost function. The maximum RMS dose excess defines the amount of violation that is acceptable. The maximum dose and/or maximum RMS dose excess may be defined by a user.

The quadratic underdose cost function is a cost function that is applied to a target volume. The quadratic underdose function implements a quadratic penalty. The cost function takes as input a minimum dose in Gy and a maximum dose deficit in Gy (i.e., the reference objective comprises two dose values). The minimum dose is the minimum dose allowable in a target and represents the dose under which a penalty is incurred. The maximum dose deficit is analogous to the maximum RMS dose excess in that it defines the amount of violation from the prescription that is acceptable.

The Serial cost function is generally used with serial OARs. Serial anatomical structures are those where high doses are harmful even if limited to small volumes. Examples include the spinal cord and bowel. This cost function applies large penalties for hot spots even if they are small in volume. The cost function takes as input an EUD in Gy and a power law exponent k (i.e., the reference objective comprises a dose value and a unitless number).

The Parallel cost function is generally used for parallel OARs. Parallel structures are those where very high doses in small volumes are tolerated, if the rest of the organ is spared. Examples are lungs, parotids, kidneys, liver. The cost function takes as input a reference dose in Gy, a mean organ damage (which is a fraction of the volume of the structure that can be sacrificed), and power law exponent k (i.e. the reference objective comprises a dose value, a relative volume, and a unitless number).

The Maximum Dose cost function is effectively a hard barrier that can be applied to target structures or OAR. The Maximum Dose cost function has a penalty that takes effect whenever voxels cross a maximum dose threshold. The cost function takes as input maximum dose in Gy (i.e., the reference objective comprises a dose value).

The Overdose DVH cost function takes as input an objective dose in Gy and a maximum volume (i.e., the reference objective comprises a dose value and a relative volume). This cost function is applied to OARs. The purpose is to keep the volume that receives more than the objective dose below the relative volume.

The Underdose DVH cost function takes as input an objective dose in Gy and a minimum volume (i.e., the reference objective comprises a dose value and a relative volume). This cost function is applied to targets. The purpose is to keep the volume of the target that receives less than the objective dose above the minimum volume.

Further details of the cost functions are provided in Monaco® Training Guide, Document ID: LTGMON0530 (Elekta AB).

Figure 2:
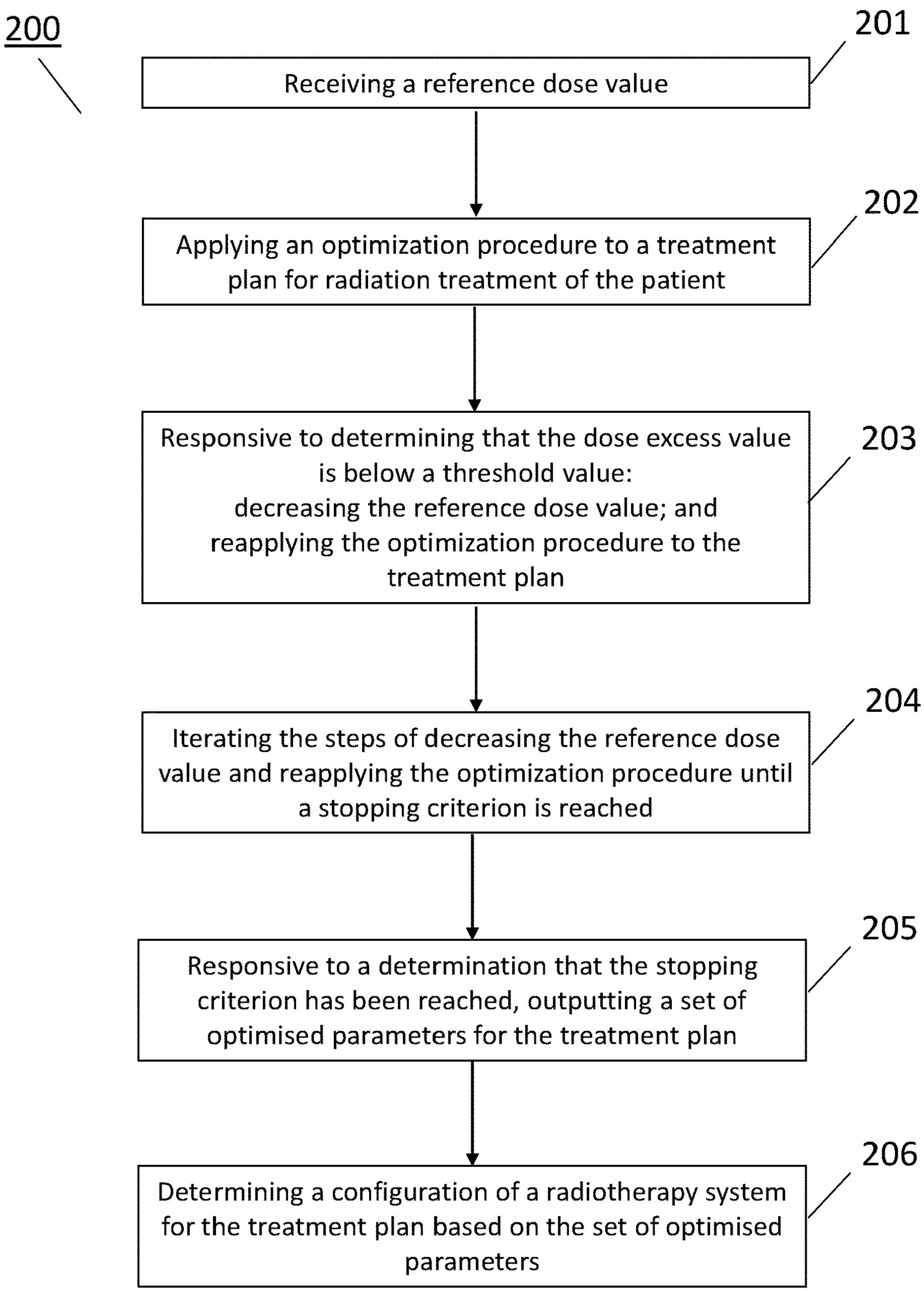
FIG. 2 is a flow chart showing a computer-implemented method according to various embodiments of the present disclosure.

The flow chart in FIG. 2 illustrates a computer-implemented method 200 for radiation treatment planning according to various embodiments of the disclosure.

The radiation treatment planning may be for radiation treatment with any type of ionising radiation, such as X-rays, electrons, protons, or ions. The radiation treatment may be, for example, IMRT, VMAT, Image-guided radiation therapy (IGRT), proton beam therapy (PBT), intensity modulated proton therapy (IMPT), or electron beam therapy (EBT). The treatment plan may be for the treatment of any part of a human or animal body.

The method 200 comprises, in step 201, receiving a reference dose value. The reference dose value is a defined maximum radiation dose within a first region for radiation treatment in a patient. The reference dose value may therefore represent a reference objective for the optimisation procedure, e.g., the reference dose value may correspond to the reference objective 104 described with respect to FIG. 1A. For example, the reference objective may be a goal to be achieved by the optimisation procedure of determining a treatment plan in which the dose delivered to the first region does not exceed the reference dose value. The reference dose value may, for example, be received in step 201 as an input by a clinician or user. For example, a clinician may select a reference dose value based on the type of tissue in the first region. The clinician or a user may pass the reference dose value to a data processing apparatus that performs the method 200 of FIG. 2.

The first region may be an anatomical region of the patient, e.g., the first region may comprise one or more of: a target region for the radiation treatment, a region of healthy tissue (OAR), a PTV, a critical structure, and a shell structure. The first region may be a subregion of a larger anatomical region that is to receive treatment. The first region may be defined by image segmentation, e.g., by performing image segmentation of a two- or three-dimensional image or model of the larger anatomical region. In some embodiments, receiving the reference dose value further comprises receiving an indication of the first region.

The method 200 further comprises, in step 202, applying an optimisation procedure to a treatment plan (e.g. a dose distribution or fluence map) for radiation treatment of the patient. The optimisation procedure seeks to minimize a cost function which is representative of a dose excess value above the reference dose value. For example, the optimisation procedure may correspond to the optimization procedure 100 described with reference to FIG. 1A. The optimisation procedure may iteratively adapt the treatment plan to minimize the cost function. Herein, the term treatment plan may refer to a dose distribution or fluence map for an anatomical region comprising the first region. The dose excess value may be an optimisable parameter for the optimisation procedure, e.g., it may correspond to (or be comprised in) the parameters 103 described with reference to FIG. 1A. In some embodiments, the dose excess value is a root mean square dose excess value.

The cost function may be a quadratic overdose cost function. For example, the cost function may be proportional to:

$$\sum\nolimits_{i \in V} |V_i| [D_i - \Delta]_+^2 \quad \text{(Eqn. 2)}$$

representing a summation over i voxels in a volume V of the first region, wherein $V_i$ is a volume of the ith voxel, $D_i$ is a dose delivered to the ith voxel, Δ is the reference dose value, and the operator $[D_i-\Delta]_+$ represents the maximum of $[D_i-\Delta]$ and zero.

The optimisation procedure may seek to minimize the cost function with respect to one or more optimisable parameters. As noted above, the dose excess value may be an optimisable parameter for the optimisation procedure. The one or more optimisable parameters may further comprise, for example, one or more of: beamlets weights, beam angles, dose-histogram-volume information, a number of radiation beams, and a dose per beam.

The received reference dose value may be a reference objective for the optimisation procedure, e.g., it may correspond to the reference objective 104 described with respect to FIG. 1A.

The reference objective for the optimisation procedure may comprise the reference dose value and a maximum dose excess value, e.g., a maximum RMS dose excess value. The maximum dose excess value is an indication of a maximum violation of the reference dose value (e.g., an amount by which the dose achieved by the treatment plan can exceed the reference dose value). For example, the maximum RMS dose excess value may indicate a maximum value for the cost function. The maximum dose excess value represents an objective for the optimisation, e.g., a goal to be achieved.

The method 200 may further comprise, prior to applying the optimization procedure, receiving the maximum dose excess value. For example, the maximum dose excess value may be determined by a user or clinician.

The reference objective for the optimisation procedure may further comprise one or more of: an indication of the first region; an indication of the cost function; a cost function value; and a priority level for the reference objective.

In some embodiments, the optimization procedure further seeks to minimise the cost function subject to one or more constraints. For example, the one or more constraints may relate to the first region and/or to one or more different (e.g., neighbouring or overlapping) anatomical regions. The one or more constraints may, for example, relate to a target for the radiation, or to an OAR. The one or more constraints may also, or instead, relate to one or more different cost functions, e.g., quadratic overdose, serial, parallel, etc. The one or more constraints may comprise a constraint that was an objective for a previous optimisation procedure and that has now been fixed as a constraint. For example, multiple optimisation procedures may be performed sequentially when generating a treatment plan. The treatment plan may be optimised with respect to higher-priority objectives first; once optimised with respect to the higher-priority objectives, the treatment plan is optimised with respect to lower-priority objectives, while the higher-priority objectives are set to constraints. In this way, the treatment plan preferentially achieves higher-priority objectives; lower-priority objectives are addressed once the higher-priority objectives have already been addressed, and to the extent that the achievement of the higher-priority objectives allows.

The optimisation procedure may output a set of optimised parameters for the treatment plan (e.g., the set of optimised parameters may correspond to the optimised parameters 111 described with respect to FIG. 1A). For example, the optimised parameters may define a fluence map for the treatment. The optimisation procedure may further output one or more of: a cost function value; an achieved radiation dose within the first region; and a dose excess value (e.g., a RMS dose excess value).

In step 203, the method 200 further comprises, responsive to determining that the dose excess value is below a threshold value, decreasing the reference dose value and reapplying the optimization procedure to the treatment plan. The optimisation procedure (when reapplied) seeks to minimise the cost function based on the decreased reference dose value. For example, the decreased reference dose value may correspond to an updated reference objective 104.

Decreasing the reference dose value prevents the cost function becoming idle (i.e., no longer contributing to the optimisation). For example, the cost function may perform well when the dose excess value is approximately within the range 0.1 to 1.0 Gy, but the cost function becomes idle when the dose excess value (and thus the cost function) is reduced to zero (or close to zero), e.g., less than 0.1 Gy. This occurs when the dose delivered to each voxel is less than the reference dose value. Decreasing the reference dose value according to the present disclosure results in an increase in the cost function. Thus, the cost function is prevented from becoming idle before the dose to be delivered to the first region has been fully optimised (i.e., reduced as far as possible within the constraints of the optimisation problem). With the decreased reference dose value, it is possible to further reduce unwanted dose within the treatment plan. Therefore, decreasing the reference dose value according to the present disclosure provides improved treatment plans.

The threshold value is equal to or less than the maximum dose excess value. In some embodiments, it is only when the maximum dose excess value is satisfied (i.e., the achieved dose excess is less than the maximum dose excess value) that the threshold value is used to determine whether to decrease the reference dose value.

The threshold value may be received by the data processing apparatus that is performing the method 200 (e.g., as a user input). Alternatively, the threshold value may be stored in memory that is comprised in, or accessible to, the data processing apparatus. Thus, the method 200 may further comprise, prior to applying the optimization procedure, receiving the threshold value.

The method 200 may further comprise, in step 204, iterating the steps of decreasing the reference dose value and reapplying the optimization procedure until a stopping criterion is reached. For each iteration, the reference dose value may be decreased by a fixed value. For example, the fixed value may be between 0.3 and 0.7 Gy (e.g., 0.5 Gy), although other values may be suitable depending on factors such as the type of treatment and the first region. Alternatively, the reference dose value may be decreased by an amount based on one or more of: the reference dose value, the threshold value, and a difference between the reference dose value and the threshold value. For example, the reference dose value for the (i+1)th iteration may be decreased by a percentage of the reference dose for the ith iteration, e.g., by 5% of the reference dose, or by any other percentage value. In some embodiments, the percentage value may be between 2% and 15% inclusive.

The computer-implemented method 200 thus converges on a better treatment plan than would otherwise be obtained. This is achieved without the need for user input and therefore provides an automated, reliable, and time-efficient method for treatment planning.

The stopping criterion may comprise the optimization procedure failing to reduce the cost function such that the dose excess value is below the threshold value. The stopping criterion may comprise the optimization procedure failing to reduce the cost function such that the dose excess value is below the threshold value after a defined number of optimization iterations or a defined amount of time. Alternatively, the stopping criterion may simply be a defined number of optimization iterations or a defined amount of time.

The method 200 may further comprise a step 205 of: responsive to a determination that the stopping criterion has been reached, outputting a set of optimised parameters for the treatment plan. The optimised parameters may, for example, be outputted for user review. Alternatively, the optimised parameters may form the input parameters (e.g., corresponding to parameters 103 of FIG. 1A) for a subsequent optimisation procedure (e.g., corresponding to method 200 of FIG. 2 and/or procedure 100 of FIG. 1A).

In some embodiments, the method 200 further comprises, in step 206, determining a configuration of a radiotherapy system for the treatment plan based on the set of optimised parameters. For example, this step may correspond to step 153 of FIG. 1B.

As noted above, the output of the method 200 of FIG. 2 may be inputted into a subsequent optimisation procedure. For example, a set of optimised parameters obtained by the method 200 may be the input parameters of a subsequent optimisation procedure (e.g., parameters 103 of FIG. 1A). Similarly, the method 200 may use as input parameters the output parameters of a previous optimisation procedure. The use of multiple optimisation procedures in treatment planning is explained further with reference to Table 1 below.

TABLE 1

Example of a wish-list

| | Clinical & Planning Constraints | | | | |
|---|---|---|---|---|---|
| row | Type | Layering order | Structure | Cost function (parameter values) | Goal |
| a | Clinical | 5 | External | Max Dose | <38 Gy |
| b | Clinical | 6 | Rectum | Parallel (32 Gy, k = 4) | <4.5% |
| c | Clinical | 6 | Rectum | Parallel (28 Gy, k = 4) | <9.5% |
| d | Clinical | 6 | Rectum | Parallel (18 Gy, k = 4) | <34.5% |
| e | Clinical | 8 | Femoral head right | Maximum Dose | <19 Gy |
| f | Clinical | 9 | Femoral head left | Maximum Dose | <19 Gy |
| g | Planning | 1 | Urethral PRV | Quadratic Overdose | <0.05 Gy |

TABLE 1-continued

| Example of a wish-list | | | | | |
|---|---|---|---|---|---|
| | | | | (35 Gy) | |
| h | Planning | 2 | PTV rectum | Quadratic Overdose (34.5 Gy) | <0.10 Gy |
| i | Planning | 3 | PTV bladder | Quadratic Overdose (34.5 Gy) | <0.04 Gy |
| j | Planning | 4 | PTV | Quadratic Overdose (37.3 Gy) | <0.02 Gy |
| k | Planning | 5 | External | Quadratic Overdose (32 Gy) | <0.09 Gy |
| l | Planning | 5 | External | Quadratic Overdose (11.5 Gy) | <0.02 Gy |

| | Prioritised Objectives | | | | |
|---|---|---|---|---|---|
| | Priority | Layering Order | Structure | Cost Function (parameter values) | Goal |
| m | 1 | 1 | Urethral PRV(a) | Target Penalty (97%) | >33.2 Gy |
| n | 1 | 2 | PTV rectum | Target Penalty (97%) | >33.2 Gy |
| o | 1 | 3 | PTV bladder | Target Penalty (95%) | >33.2 Gy |
| p | 1 | 4 | PTV | Target Penalty (97%) | >35 Gy |
| q | 1 | 4 | PTV | Target Penalty (99.5%) | >33.2 Gy |
| r | 2 | 6 | Rectum | Parallel (28 Gy, k = 4) | <1% |
| s | 3 | 6 | Rectum | Serial (k = 1) | <10% |
| t | 4 | 6 | Rectum | Parallel (18 Gy, k = 4) | <20% |
| u | 5 | 7 | Bladder | Serial (k = 1) | <12 Gy |
| v | 7 | 10 | Penile bulb | Serial (k = 1) | <2Gy |
| w | 8 | 8 | Femoral head right | Quadratic Overdose (15 Gy) | <0.5Gy |
| x | 8 | 9 | Femoral head left | Quadratic Overdose (15 Gy) | <0.5 Gy |

Table 1 is an example of part of a clinical prescription, also referred to as a wish-list, for a radiation treatment plan for the treatment of prostate cancer. The wish-list defines what is desired to be achieved by the treatment plan and may be defined by a user. A wish-list comprises one or more constraints (rows 1 to l of Table 1) and/or one or more objectives (rows m to x of Table 1). Here, each objective (i.e., each row of rows m to x) corresponds to a reference objective 104 described with respect to FIG. 1A. Alternatively (not shown in table 1), any of the objectives of Table 1 could instead be formulated as a constraint. The constraints (i.e., each row of rows a to l) corresponds to a constraint 105 described with respect to FIG. 1A.

The wish-list shown in Table 1 comprises the 'clinical' constraints (rows a to f). The wish-list further comprises 'planning' constraints (rows g to l). The purpose of 'planning' constraints is to achieve dose conformality and control of potential hotspots.

The clinical constraints and planning constraints are predefined constraints. These constraints cannot be violated, and therefore the violation of any one of these constraints results in plan rejection. The purpose of constraints in rows a to l is to limit the dose at the corresponding structures.

The wish-lists further comprises prioritised objectives (row m to x). The priority for each objective is given in the second column. The prioritised objectives correspond to the reference objective described with respect to FIG. 1A. The prioritized objectives comprise: objectives that relate to the dose coverage and conformality of the target (which are the 1st-priority objectives in rows m to q), and objectives that are concerned with dose sparing of the OARs (rows r to y).

The priority refers to the relative priority of the reference objectives. In Table 1, the objectives that relate to dose coverage and conformality of the target (which are the 1st-priority objectives in rows m to q) are optimised first, and objectives that are concerned with dose sparing of the OARs (rows r to y) are optimised after, in order of their priorities. The priority values may be user-defined priorities.

The fourth column of Table 1 gives the name of the structure (i.e., the anatomical region) to which the constrain or objective relates. Thus, the structure name represents an anatomical structure. The structures are obtained by a process known as segmentation, where contours are drawn on a slice of an MRI image or a CT image to identify the different structures. The contour may be generated manually (e.g., by a physician, dosimetrist, or health care worker) or automatically using an Atlas-based auto-segmentation software.

In Table 1, the "Cost function (parameter values)" relates to the type of cost function to be used. For some cost functions, additional parameters are provided. The 'Goal' refers to a goal to be achieved by the treatment planning system.

For example, at row m, the reference objective is for 97% of the Urethral PRV(a) to achieve a dose of 33.2 Gy. The cost function associated to said reference objective is a 'Target Penalty'.

For each structure, one or more cost functions and associated goals, each achieving different purposes, is defined. For example, at rows r to t, for the 'Rectum' structure, different cost functions and goals are applied.

In Table 1, the layering order relates to structure volumes that overlap. When structures comprise overlapping voxels, the structure with the higher layering order 'owns' the voxel, e.g., the voxel is only included in cost functions associated with that structure. The voxel is not included in any cost function associated with structures with lower layering order (i.e., structures that do not 'own' the voxel).

A further example of a wish-list is provided in Naccarato, S., Rigo, M., Pellegrini, R., Voet, P., Akhiat, H., Gurrera, D., De Simone, A., Sicignano, G., Mazzola, R., Figlia, V. and Ricchetti, F., 2022. Automated planning for prostate stereotactic body radiation therapy on the 1.5 T MR-Linac. Advances in radiation oncology, 7 (3), p. 100865.

Figure 3:
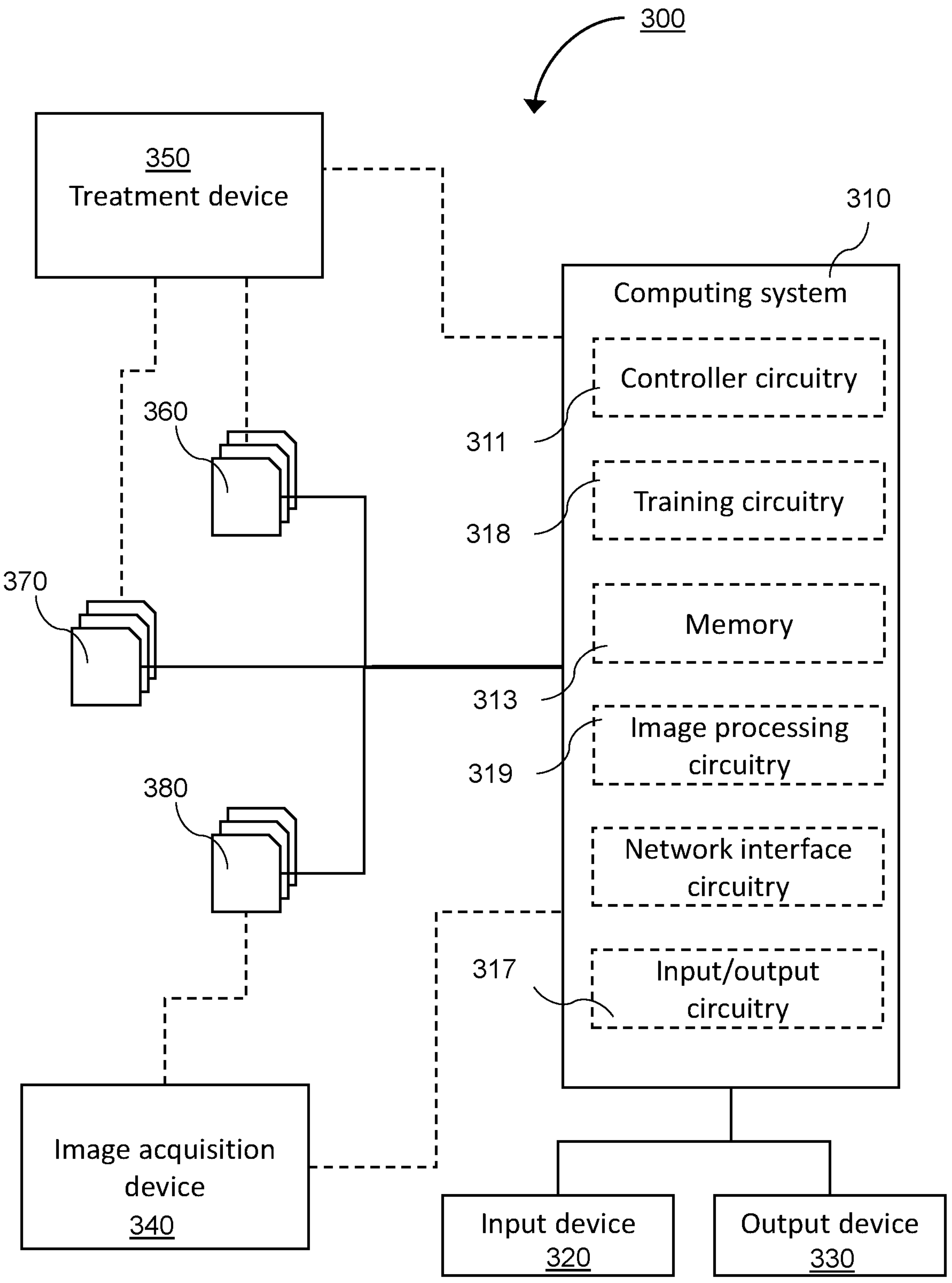
FIG. 3 is a schematic illustration of a computing device according to various embodiments of the present disclosure.

FIG. 3 illustrates a block diagram of an implementation of a radiotherapy system 300. The radiotherapy system 300 comprises a computing system 310 within which a set of instructions, for causing the computing system 310 to perform any one or more of the methods discussed herein, may be executed. The computing system 310 may implement a treatment planning system. The computing system 310 may also be referred to as a computer. The treatment planning system 310 may perform any of the methods described herein. In particular, the methods described herein may be implemented by a processor 311 of the treatment planning system 310.

The computing system 310 shall be taken to include any number or collection of machines, e.g. computing device(s), that individually or jointly execute a set (or multiple sets) of instructions to perform any one or more of the methods discussed herein. That is, hardware and/or software may be provided in a single computing device, or distributed across a plurality of computing devices in the computing system. In some implementations, one or more elements of the computing system may be connected (e.g., networked) to other machines, for example in a Local Area Network (LAN), an intranet, an extranet, or the Internet. One or more elements of the computing system may operate in the capacity of a server or a client machine in a client-server network environment, or as a peer machine in a peer-to-peer (or distributed) network environment. One or more elements of the computing system may be a personal computer (PC), a tablet computer, a set-top box (STB), a Personal Digital Assistant (PDA), a cellular telephone, a web appliance, a server, a network router, switch or bridge, or any machine capable of executing a set of instructions (sequential or otherwise) that specify actions to be taken by that machine.

The computing system 310 includes controller circuitry 311 and a memory 313 (e.g., read-only memory (ROM), flash memory, dynamic random access memory (DRAM) such as synchronous DRAM (SDRAM) or Rambus DRAM (RDRAM), etc.). The memory 313 may comprise a static memory (e.g., flash memory, static random access memory (SRAM), etc.), and/or a secondary memory (e.g., a data storage device), which communicate with each other via a bus (not shown).

Controller circuitry 311 represents one or more general-purpose processors such as a microprocessor, central processing unit, accelerated processing units, or the like. More particularly, the controller circuitry 311 may comprise a complex instruction set computing (CISC) microprocessor, reduced instruction set computing (RISC) microprocessor, very long instruction word (VLIW) microprocessor, processor implementing other instruction sets, or processors implementing a combination of instruction sets. Controller circuitry 311 may also include one or more special-purpose processing devices such as an application specific integrated circuit (ASIC), a field programmable gate array (FPGA), a digital signal processor (DSP), network processor, or the like. One or more processors of the controller circuitry may have a multicore design. Controller circuitry 311 is configured to execute the processing logic for performing the operations and steps discussed herein.

The computing system 310 may further include a network interface circuitry 318. The computing system 310 may be communicatively coupled to an input device 320 and/or an output device 330, via input/output circuitry 317. In some implementations, the input device 320 and/or the output device 330 may be elements of the computing system 310. The input device 320 may include an alphanumeric input device (e.g., a keyboard or touchscreen), a cursor control device (e.g., a mouse or touchscreen), an audio device such as a microphone, and/or a haptic input device. The output device 330 may include an audio device such as a speaker, a video display unit (e.g., a liquid crystal display (LCD) or a cathode ray tube (CRT)), and/or a haptic output device. In some implementations, the input device 320 and the output device 330 may be provided as a single device, or as separate devices.

In some implementations, the computing system 310 may comprise image processing circuitry 319. Image processing circuitry 319 may be configured to process image data 380 (e.g. images, or imaging data), such as medical images obtained from one or more imaging data sources, a treatment device 350 and/or an image acquisition device 340. Image processing circuitry 319 may be configured to process, or pre-process, image data. For example, image processing circuitry 319 may convert received image data into a particular format, size, resolution or the like. In some implementations, image processing circuitry 319 may be combined with controller circuitry 311.

Figure 5:
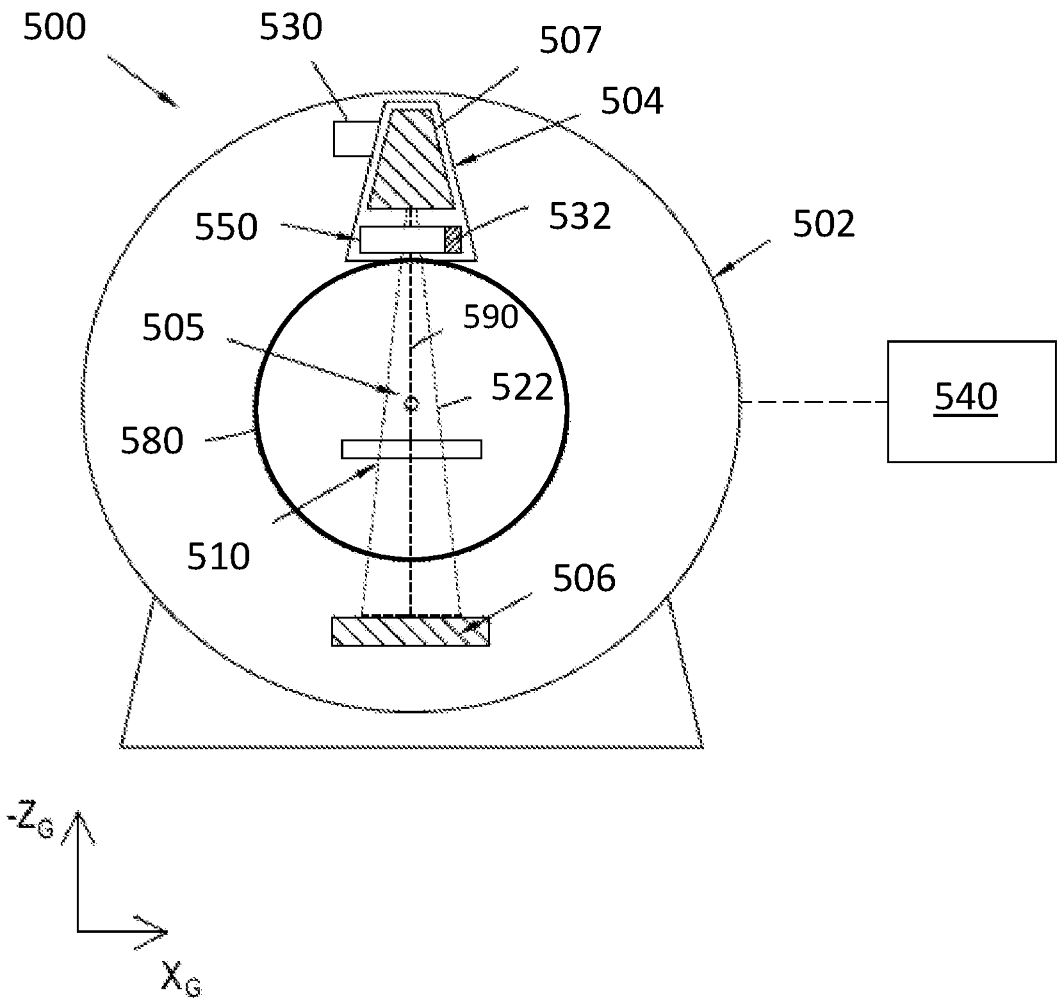
FIG. 5 is a schematic illustration of a radiotherapy apparatus.

In some implementations, the radiotherapy system 300 may further comprise an image acquisition device 340 and/or a treatment device 350, such as those disclosed herein in the examples of FIG. 5. The image acquisition device 340 and the treatment device 350 may be provided as a single device. In some implementations, treatment device 350 is configured to perform imaging, for example in addition to providing treatment and/or during treatment. The treatment device 350 comprises the main radiation delivery components of the radiotherapy system, such as beam shaping apparatus 550.

Image acquisition device 340 may be configured to perform positron emission tomography (PET), computed tomography (CT), magnetic resonance imaging (MRI), single positron emission computed tomography (SPECT), x-ray, and the like.

Image acquisition device 340 may be configured to output image data 380, which may be accessed by computing system 310. Treatment device 350 may be configured to output treatment data 360, which may be accessed by computing system 310.

Computing system 310 may be configured to access or obtain treatment data 360, planning data 370 and/or image data 380. Treatment data 360 may be obtained from an internal data source (e.g. from memory 313) or from an external data source, such as treatment device 350 or an external database. Planning data 370 may be obtained from memory 313 and/or from an external source, such as a planning database. Planning data 370 may comprise information obtained from one or more of the image acquisition device 340 and the treatment device 350.

Figure 4:
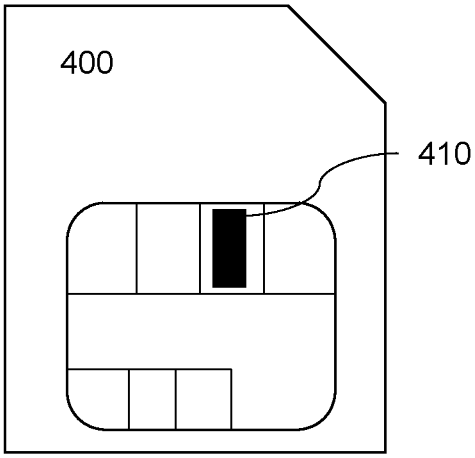
FIG. 4 is a schematic illustration of a computer-readable medium according to various embodiments of the present disclosure.

FIG. 4 is a schematic illustrating a computer program product 400 according to some embodiments. The various methods described above may be implemented by a computer program. The computer program may include computer code (e.g. instructions) 410 arranged to instruct a computer to perform the method 200 described with respect to FIG. 2.

For example, the steps of the methods described in relation to FIG. 2 may be performed by the computer code 410. The steps of the methods described above may be performed in any suitable order. The computer program and/or the code 410 for performing such methods may be provided to an apparatus, such as a computer, on one or more computer readable media or, more generally, a computer program product 400)), depicted in FIG. 4. The computer readable media may be transitory or non-transitory. The one or more computer readable media 400 could be, for example, an electronic, magnetic, optical, electromagnetic, infrared, or semiconductor system, or a propagation medium for data transmission, for example for downloading the code over the Internet. Alternatively, the one or more computer readable media could take the form of one or more physical computer readable media such as semiconductor or solid state memory, magnetic tape, a removable computer diskette, a random access memory (RAM), a read-only memory (ROM), a rigid magnetic disc, and an optical disk, such as a CD-ROM, CD-R/W or DVD. The instructions 410 may also reside, completely or at least partially, within the memory 313 and/or within the controller circuitry 311 during execution thereof by the computing system 310, the memory 313 and the controller circuitry 311 also constituting computer-readable storage media.

In an implementation, the modules, components and other features described herein can be implemented as discrete components or integrated in the functionality of hardware components such as ASICS, FPGAs, DSPs or similar devices.

A "hardware component" is a tangible (e.g., non-transitory) physical component (e.g., a set of one or more processors) capable of performing certain operations and may be configured or arranged in a certain physical manner. A hardware component may include dedicated circuitry or logic that is permanently configured to perform certain operations. A hardware component may comprise a special-purpose processor, such as an FPGA or an ASIC. A hardware component may also include programmable logic or circuitry that is temporarily configured by software to perform certain operations.

In addition, the modules and components can be implemented as firmware or functional circuitry within hardware devices. Further, the modules and components can be implemented in any combination of hardware devices and software components, or only in software (e.g., code stored or otherwise embodied in a machine-readable medium or in a transmission medium).

FIG. 5 depicts a radiotherapy apparatus according to the present disclosure. FIG. 5 shows a cross-section through a radiotherapy apparatus 500 comprising a radiation head 504 and a beam receiving apparatus 506, both of which are attached to a gantry 502. The radiation head 504 includes a radiation source 507 which emits a beam of radiation 522. The radiation head 504 also includes a beam shaping apparatus 550 which controls the size and shape of the radiation field associated with the beam.

The beam receiving apparatus 506 is configured to receive radiation emitted from the radiation head 504, for the purpose of absorbing and/or measuring the beam of radiation. In the view shown in FIG. 5, the radiation head 504 and the beam receiving apparatus 506 are positioned diametrically opposed to one another.

The gantry 502 is rotatable, and supports the radiation head 504 and the beam receiving apparatus 506 such that they are rotatable around an axis of rotation 505, which may coincide with the patient longitudinal axis. As shown in FIG. 5, the gantry provides rotation of the radiation head 504 and the beam receiving apparatus 506 in a plane which is perpendicular to the patient longitudinal axis (e.g. a sagittal plane). Three gantry directions XG, YG, ZG can be defined, where the YG direction is perpendicular with gantry axis of rotation. The ZG direction extends from a point on the gantry corresponding to the radiation head, towards the axis of rotation of the gantry. Therefore, from the patient frame of reference, the ZG direction rotates around as the gantry rotates.

FIG. 5 also shows a support surface 510 on which a subject (or patient) is supported during radiotherapy treatment. The radiation head 504 is configured to rotate around the axis of rotation 505 such that the radiation head 504 directs radiation towards the subject from various angles around the subject in order to spread out the radiation dose received by healthy tissue to a larger region of healthy tissue while building up a prescribed dose of radiation at a target region.

The radiotherapy apparatus 500 is configured to deliver a radiation beam towards a radiation isocentre which is substantially located on the axis of rotation 505 at the centre of the gantry 502 regardless of the angle at which the radiation head 504 is placed.

The rotatable gantry 502 and radiation head 504 are dimensioned so as to allow a central bore 580 to exist. The central bore 580 provides opening sufficient to allow a subject to be positioned therethrough without the possibility of being incidentally contacted by the radiation head 504 or other mechanical components as the gantry rotates the radiation head 504 about the subject.

As shown in FIG. 5, the radiation head 504 emits the radiation beam 522 along a beam axis 590 (or radiation axis or beam path), where the beam axis 590 is used to define the direction in which the radiation is emitted by the radiation head. The radiation beam 522 is incident on the beam receiving apparatus 506 which can include at least one of a beam stopper and a radiation detector. The beam receiving apparatus 506 is attached to the gantry 502 on a diametrically opposite side to the radiation head 504 to attenuate and/or detect a beam of radiation after the beam has passed through the subject.

The radiation beam axis 590 may be defined as, for example, a centre of the radiation beam 522 or a point of maximum intensity.

The beam shaping apparatus 550 delimits the spread of the radiation beam 522. The beam shaping apparatus 550 is configured to adjust the shape and/or size of a field of radiation produced by the radiation source. The beam shaping apparatus 550 does this by defining an aperture (also referred to as a window or an opening) of variable shape to collimate the radiation beam 522 to a chosen cross-sectional shape. In this example, the beam shaping apparatus 550 may be provided by a combination of a diaphragm and a multi-leaf collimator (MLC). Beam shaping apparatus 550 may also be referred to as a bean modifier.

The radiotherapy apparatus 500 may be configured to deliver both coplanar and non-coplanar (also referred to as tilted) modes of radiotherapy treatment. In coplanar treatment, radiation is emitted in a plane which is perpendicular to the axis of rotation of the radiation head 504. In non-coplanar treatment, radiation is emitted at an angle which is not perpendicular to the axis of rotation. In order to deliver coplanar and non-coplanar treatment, the radiation head 504 can move between at least two positions, one in which the radiation is emitted in a plane which is perpendicular to the axis of rotation (coplanar configuration) and one in which radiation is emitted in a plane which is not perpendicular to the axis of rotation (non-coplanar configuration).

In the coplanar configuration, the radiation head is positioned to rotate about a rotation axis and in a first plane. In the non-coplanar configuration, the radiation head is tilted with respect to the first plane such that a field of radiation produced by the radiation head is directed at an oblique angle relative to the first plane and the rotation axis. In the non-coplanar configuration, the radiation head is positioned to rotate in a respective second plane parallel to and displaced from the first plane. The radiation beam is emitted at an oblique angle with respect to the second plane, and therefore as the radiation head rotates the beam sweeps out a cone shape.

The beam receiving apparatus 506 remains in the same place relative to the rotatable gantry when the radiotherapy apparatus is in both the coplanar and non-coplanar modes. Therefore, the beam receiving apparatus 506 is configured to rotate about the rotation axis in the same plane in both coplanar and non-coplanar modes. This may be the same plane as the plane in which the radiation head rotates.

The beam shaping apparatus 550 is configured to reduce the spread of the field of radiation in the non-coplanar configuration in comparison to the coplanar configuration.

The radiotherapy apparatus 500 includes a controller 540 which is programmed to control the radiation source 507, beam receiving apparatus 506 and the gantry 502. Controller 540 may perform functions or operations such as treatment planning, treatment execution, image acquisition, image processing, motion tracking, motion management, and/or other tasks involved in a radiotherapy process.

Controller 540 is programmed to control features of apparatus 500 according to a radiotherapy treatment plan for irradiating a target region, also referred to as a target tissue, of a patient. The treatment plan includes information about a particular dose to be applied to a target tissue, as well as other parameters such as beam angles, dose-histogram-volume information, the number of radiation beams to be used during therapy, the dose per beam, and the like. Controller 540 is programmed to control various components of apparatus 500, such as gantry 502, radiation head 504, beam receiving apparatus 506, and support surface 510, according to the treatment plan.

Hardware components of controller 540 may include one or more computers (e.g., general purpose computers, workstations, servers, terminals, portable/mobile devices, etc.); processors (e.g., central processing units (CPUs), graphics processing units (GPUs), microprocessors, digital signal processors (DSPs), field programmable gate arrays (FPGAs), special-purpose or specially-designed processors, etc.); memory/storage devices such as a memory (e.g., read-only memories (ROMs), random access memories (RAMs), flash memories, hard drives, optical disks, solid-state drives (SSDs), etc.); input devices (e.g., keyboards, mice, touch screens, mics, buttons, knobs, trackballs, levers, handles, joysticks, etc.); output devices (e.g., displays, printers, speakers, vibration devices, etc.); circuitries; printed circuit boards (PCBs); or other suitable hardware. Software components of controller 140 may include operation device software, application software, etc.

The radiation head 504 may be connected to a head actuator 530 which is configured to actuate the radiation head 504, for example between a coplanar configuration and one or more non-coplanar configurations. This may involve translation and rotation of the radiation head 504 relative to the gantry. In some implementations, the head actuator may include a curved rail along which the radiation head 504 may be moved to adjust the position and angle of the radiation head 504. The controller 540 may control the configuration of the radiation head 504 via the head actuator 530.

The beam shaping apparatus 550 includes a shaping actuator 532. The shaping actuator is configured to control the position of one or more elements in the beam shaping apparatus 550 in order to shape the radiation beam 522. In some implementations, the beam shaping apparatus 550 includes an MLC, and the shaping actuator 532 includes means for actuating leaves of the MLC. The beam shaping apparatus 550 may further comprise a diaphragm, and the shaping actuator 532 may include means for actuating blocks of the diaphragm. The controller 540 may control the beam shaping apparatus 550 via the shaping actuator 532.

A treatment plan may comprise positioning information of beam shaping apparatus 550. The positioning information of beam shaping apparatus 550 may comprise information indicating a configuration of one or more elements of beam shaping apparatus 550, such as leaf configuration of an MLC of beam shaping apparatus 550, a configuration of a diaphragm of beam shaping apparatus 550, a configuration of an opening (e.g., window or aperture) of the MLC, and/or the like.

As described herein, the purpose of an optimiser (or of an optimisation procedure) is to find a set of optimised parameters for which a cost function is minimised. However, it will be understood that, alternatively and equivalently, the purpose of the optimiser (or of the optimisation procedure) may be taken to be to find a set of optimised parameters for which a reward function is maximised.

Unless specifically stated otherwise, as apparent from the following discussion, it is appreciated that throughout the description, discussions utilizing terms such as "receiving", "determining", "comparing", "enabling", "maintaining," "identifying,", "obtaining", "accessing" or the like, refer to the actions and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

While certain embodiments have been described, these embodiments have been presented by way of example only, and are not intended to limit the scope of the claims appended hereto. Indeed, the novel methods and apparatus described herein may be embodied in a variety of other forms; furthermore, various omissions, substitutions and changes in the form of methods and apparatus described herein may be made.

The following numbered statements set out embodiments of the disclosure:

1. A computer-implemented method for radiation treatment planning, the method comprising:
   - receiving a reference dose value, wherein the reference dose value is a defined maximum radiation dose within a first region for radiation treatment in a patient;
   - applying an optimization procedure to a treatment plan for radiation treatment of the patient, wherein the optimization procedure seeks to minimize a cost function which is representative of a dose excess value above the reference dose value; and
   - responsive to determining that the dose excess value is below a threshold value:
     - decreasing the reference dose value; and
     - reapplying the optimization procedure to the treatment plan, wherein the optimization procedure seeks to minimize the cost function based on the decreased reference dose value.
2. The method of embodiment 1, further comprising iterating the steps of decreasing the reference dose value and reapplying the optimization procedure until a stopping criterion is reached.
3. The method of embodiment 2, wherein the stopping criterion comprises the optimization procedure failing to reduce the cost function such that the dose excess value is below the threshold value.
4. The method of embodiment 3, wherein the stopping criterion comprises the optimization procedure failing to reduce the cost function such that the dose excess value is below the threshold value after a defined number of optimization iterations or a defined amount of time.
5. The method of any one of embodiments 2 to 4, further comprising, responsive to a determination that the stopping criterion has been reached, outputting a set of optimised parameters for the treatment plan.
6. The method of embodiment 5, wherein the set of optimised parameters define a fluence map for the treatment plan.

7. The method of embodiment 5 or 6, further comprising determining a configuration of a radiotherapy system for the treatment plan based on the set of optimised parameters.
8. The method of any one of the preceding embodiments, wherein the optimization procedure iteratively adapts the treatment plan to minimize the cost function.
9. The method of any one of the preceding embodiments, wherein the reference dose value is decreased by a fixed value.
10. The method of embodiment 9, wherein the fixed value is between 0.3 and 0.7 Gy.
11. The method of any one of embodiments 1 to 8, wherein the reference dose value is decreased by an amount based on one or more of: the reference dose value, the threshold value, and a difference between the reference dose value and the threshold value.
12. The method of any one of the preceding embodiments, wherein the dose excess value comprises a root mean square dose excess value.
13. The method of any one of the preceding embodiments, wherein the cost function is a quadratic overdose cost function.
14. The method of embodiment 13, wherein the cost function is proportional to:

$$\sum_{i \in V} |V_i| [D_i - \Delta]_+^2$$

representing a summation over i voxels in a volume V of the first region, wherein $V_i$ is a volume of the ith voxel, $D_i$ is a dose delivered to the ith voxel, $\Delta$ is the reference dose value, and the operator $[D_i - \Delta]_+$ represents the maximum of $[D_i - \Delta]$ and zero.
15. The method of any preceding embodiment, wherein the method further comprises:
prior to applying the optimization procedure, receiving a maximum dose excess value, wherein the threshold value is equal to or less than the maximum dose excess value.
16. The method of embodiment 15, wherein a reference objective for the optimisation procedure comprises the reference dose value and the maximum dose excess.
17. The method of any preceding embodiment, wherein the optimization procedure further seeks to minimize the cost function subject to one or more constraints.
18. The method of any preceding embodiment, wherein the optimization procedure seeks to minimize the cost function with respect to one or more optimisable parameters.
19. The method of embodiment 18, wherein the one or more optimisable parameters comprise one or more of: the dose excess value, beamlets weights, beam angles, dose-histogram-volume information, a number of radiation beams, and a dose per beam.
20. The method of any preceding embodiment, wherein the first region comprises a target region for the radiation treatment and/or an organ at risk, OAR.
21. A data processing apparatus comprising:
a memory storing computer-executable instructions; and
a processor configured to execute the instructions to carry out the method of any of embodiments 1 to 20.
22. A computer program comprising instructions which, when the program is executed by a computer, cause the computer to carry out the method of any of embodiments 1 to 20.
23. A non-transitory computer-readable storage medium comprising instructions which, when executed by a computer, cause the computer to carry out the method of any of embodiments 1 to 20.

What is claimed is:

1. A computer-implemented method for radiation treatment planning, the method comprising:
receiving a reference dose value, wherein the reference dose value is a defined maximum radiation dose within a first region for radiation treatment in a patient;
applying an optimization procedure to a treatment plan for radiation treatment of the patient, wherein the optimization procedure reduces a cost function which is representative of a dose excess value above the reference dose value; and
responsive to determining that the dose excess value is below a threshold value:
decreasing the reference dose value;
reapplying the optimization procedure to the treatment plan, wherein the optimization procedure further reduces the cost function based on the decreased reference dose value; and
iterating the steps of decreasing the reference dose value and reapplying the optimization procedure until a stopping criterion is reached, wherein the stopping criterion comprises the optimization procedure failing to reduce the cost function such that the dose excess value is below the threshold value after a defined number of optimization iterations or a defined amount of time.

2. The method of claim 1, further comprising:
responsive to a determination that the stopping criterion has been reached, outputting a set of optimized parameters for the treatment plan.

3. The method of claim 2, wherein the set of optimized parameters define a fluence map for the treatment plan.

4. The method of claim 2, further comprising:
determining a configuration of a radiotherapy system for the treatment plan based on the set of optimized parameters.

5. The method of claim 1, wherein the optimization procedure iteratively adapts the treatment plan to minimize the cost function.

6. The method of claim 1, wherein the reference dose value is decreased by a fixed value.

7. The method of claim 6, wherein the fixed value is between 0.3 and 0.7 Gy.

8. The method of claim 1, wherein the reference dose value is decreased by an amount based on one or more of: the reference dose value, the threshold value, and a difference between the reference dose value and the threshold value.

9. The method of claim 1, wherein the dose excess value comprises a root mean square dose excess value.

10. The method of claim 1, wherein the cost function is a quadratic overdose cost function.

11. The method of claim 1, wherein the cost function is proportional to:

$$\sum_{i \in V} |V_i| [D_i - \Delta]_+^2$$

representing a summation over i voxels in a volume V of the first region, wherein $V_i$ is a volume of the ith voxel, $D_i$ is a dose delivered to the ith voxel, $\Delta$ is the reference dose value, and the operator $[D_i - \Delta]_+$ represents the maximum of $[D_i - \Delta]$ and zero.

12. The method of claim 1, wherein the method further comprises:

prior to applying the optimization procedure, receiving a maximum dose excess value, wherein the threshold value is equal to or less than the maximum dose excess value.

13. The method of claim 12, wherein a reference objective for the optimization procedure comprises the reference dose value and the maximum dose excess value.

14. The method of claim 1, wherein the optimization procedure further reduces the cost function subject to one or more constraints.

15. The method of claim 1, wherein the optimization procedure further reduces the cost function with respect to one or more optimizable parameters.

16. The method of claim 15, wherein the one or more optimizable parameters comprise one or more of: the dose excess value, one or more beamlets weights, one or more beam angles, a dose-histogram-volume information, a number of radiation beams, and a dose per beam.

17. The method of claim 1, wherein the first region comprises a target region for the radiation treatment and/or an organ at risk, OAR.

18. A data processing apparatus comprising:

a memory storing computer-executable instructions; and a processor configured to execute the instructions to:

receive a reference dose value, wherein the reference dose value is a defined maximum radiation dose within a first region for radiation treatment in a patient;

apply an optimization procedure to a treatment plan for radiation treatment of the patient, wherein the optimization procedure reduces a cost function which is representative of a dose excess value above the reference dose value; and responsive to determining that the dose excess value is below a threshold value:

decrease the reference dose value;

reapply the optimization procedure to the treatment plan, wherein the optimization procedure further reduces the cost function based on the decreased reference dose value; and iterate the steps of decreasing the reference dose value and reapplying the optimization procedure until a stopping criterion is reached, wherein the stopping criterion comprises the optimization procedure failing to reduce the cost function such that the dose excess value is below the threshold value after a defined number of optimization iterations or a defined amount of time.

19. A non-transitory computer-readable storage medium comprising instructions which, when executed by a computer, cause the computer to:

receive a reference dose value, wherein the reference dose value is a defined maximum radiation dose within a first region for radiation treatment in a patient;

apply an optimization procedure to a treatment plan for radiation treatment of the patient, wherein the optimization procedure reduces a cost function which is representative of a dose excess value above the reference dose value; and responsive to determining that the dose excess value is below a threshold value:

decrease the reference dose value;

reapply the optimization procedure to the treatment plan, wherein the optimization procedure further reduces the cost function based on the decreased reference dose value; and iterating the steps of decreasing the reference dose value and reapplying the optimization procedure until a stopping criterion is reached, wherein the stopping criterion comprises the optimization procedure failing to reduce the cost function such that the dose excess value is below the threshold value after a defined number of optimization iterations or a defined amount of time.

20. A computer-implemented method for radiation treatment planning, the method comprising:

receiving a reference dose value, wherein the reference dose value is a defined maximum radiation dose within a first region for radiation treatment in a patient;

applying an optimization procedure to a treatment plan for radiation treatment of the patient, wherein the optimization procedure reduces a cost function which is representative of a dose excess value above the reference dose value; and responsive to determining that the dose excess value is below a threshold value:

decreasing the reference dose value;

reapplying the optimization procedure to the treatment plan, wherein the optimization procedure further reduces the cost function based on the decreased reference dose value; and iterating the steps of decreasing the reference dose value and reapplying the optimization procedure until a stopping criterion is reached, wherein the stopping criterion comprises the optimization procedure failing to reduce the cost function such that the dose excess value is below the threshold value.

21. A computer-implemented method for radiation treatment planning, the method comprising:

receiving a reference dose value, wherein the reference dose value is a defined maximum radiation dose within a first region for radiation treatment in a patient;

applying an optimization procedure to a treatment plan for radiation treatment of the patient, wherein the optimization procedure reduces a cost function which is representative of a dose excess value above the reference dose value; and responsive to determining that the dose excess value is below a threshold value:

decreasing the reference dose value;

reapplying the optimization procedure to the treatment plan, wherein the optimization procedure further reduces the cost function based on the decreased reference dose value;

iterating the steps of decreasing the reference dose value and reapplying the optimization procedure until a stopping criterion is reached; and responsive to a determination that the stopping criterion has been reached, outputting a set of optimized parameters for the treatment plan, wherein the set of optimized parameters define a fluence map for the treatment plan.

22. A computer-implemented method for radiation treatment planning, the method comprising:

receiving a reference dose value, wherein the reference dose value is a defined maximum radiation dose within a first region for radiation treatment in a patient;

applying an optimization procedure to a treatment plan for radiation treatment of the patient, wherein the optimization procedure reduces a cost function which is representative of a dose excess value above the reference dose value, wherein the dose excess value comprises a root mean square dose excess value; and responsive to determining that the dose excess value is below a threshold value:

decreasing the reference dose value; and reapplying the optimization procedure to the treatment plan, wherein the optimization procedure further reduces the cost function based on the decreased reference dose value.

23. A computer-implemented method for radiation treatment planning, the method comprising:

receiving a reference dose value, wherein the reference dose value is a defined maximum radiation dose within a first region for radiation treatment in a patient;

applying an optimization procedure to a treatment plan for radiation treatment of the patient, wherein the optimization procedure reduces a cost function which is representative of a dose excess value above the reference dose value, wherein the cost function is a quadratic overdose cost function; and responsive to determining that the dose excess value is below a threshold value:

decreasing the reference dose value; and reapplying the optimization procedure to the treatment plan, wherein the optimization procedure further reduces the cost function based on the decreased reference dose value.

* * * * *